United States Patent
Peer et al.

(10) Patent No.: US 12,115,521 B2
(45) Date of Patent: Oct. 15, 2024

(54) CATALYSTS AND PROCESSES FOR CONVERTING AROMATICS

(71) Applicant: ExxonMobil Chemical Patents Inc., Baytown, TX (US)

(72) Inventors: Maryam Peer, Annandale, NJ (US); Joseph E. Gatt, Annandale, NJ (US); Preeti Kamakoti, Berkeley Heights, NJ (US); William J. Knaeble, Bridgewater, NJ (US); Wenyih F. Lai, Bridgewater, NJ (US); Paul Podsiadlo, Humble, TX (US); Dominick A. Zurlo, Easton, PA (US); Thomas J. Ferro, Bethlehem, PA (US); Doron Levin, Highland Park, NJ (US); Benjamin C. Gamoke, Collingswood, NJ (US)

(73) Assignee: ExxonMobil Engineering & Technology Company, Baytown, TX (US)

( * ) Notice: Subject to any disclaimer, the term of this patent is extended or adjusted under 35 U.S.C. 154(b) by 296 days.

(21) Appl. No.: 17/436,121

(22) PCT Filed: Mar. 26, 2020

(86) PCT No.: PCT/US2020/025016
§ 371 (c)(1),
(2) Date: Sep. 3, 2021

(87) PCT Pub. No.: WO2020/205441
PCT Pub. Date: Oct. 8, 2020

(65) Prior Publication Data
US 2022/0126278 A1 Apr. 28, 2022

Related U.S. Application Data

(60) Provisional application No. 62/826,116, filed on Mar. 29, 2019.

(30) Foreign Application Priority Data

Jul. 9, 2019 (EP) ..................... 19185107

(51) Int. Cl.
*B01J 29/40* (2006.01)
*B01J 29/18* (2006.01)
(Continued)

(52) U.S. Cl.
CPC .............. *B01J 29/40* (2013.01); *B01J 29/18* (2013.01); *B01J 29/80* (2013.01); *B01J 35/613* (2024.01);
(Continued)

(58) Field of Classification Search
None
See application file for complete search history.

(56) References Cited

U.S. PATENT DOCUMENTS 5,407,880 A 4/1995 Ikeda et al.
5,942,651 A 8/1999 Beech, Jr. et al.
(Continued)

FOREIGN PATENT DOCUMENTS

EP 0141514 5/1985
JP H07155613 6/1995
WO WO-2016126443 A1 * 8/2016 ............. B01J 29/20

OTHER PUBLICATIONS

IZA (Framework Type MEL). https://europe.iza-structure.org/IZA-SC/material_rm.php?STC=MEL. Retrieved 2024. (Year: 2024).*

*Primary Examiner* — In Suk C Bullock
*Assistant Examiner* — Alyssa L Cepluch (57) ABSTRACT

Methods and corresponding catalysts are provided for conversion of an aromatics feed containing $C_{8+}$ aromatics, particularly $C_{9+}$ aromatics, to form a converted product mixture comprising, e.g., benzene and/or xylenes. The aromatic feed can be converted in the presence of a catalyst that
(Continued)

includes a mixture of a first zeolite having an MEL framework, such as ZSM-11, and a second zeolite having a MOR framework, such as mordenite, particularly a mordenite synthesized using TEA or MTEA as a structure directing agent. The weight ratio of the first zeolite to the second zeolite in the catalyst can be from 0.3 to 1.2, or from 0.3 to 1.1, or from 0.3 to 1.0. The catalyst can further include one or more metals supported on the catalyst, such as a combination of metals.

10 Claims, 2 Drawing Sheets

(51) Int. Cl.
  *B01J 29/80* (2006.01)
  *B01J 35/61* (2024.01)
  *B01J 37/00* (2006.01)
  *C07C 6/12* (2006.01)
(52) U.S. Cl.
  CPC ........... *B01J 37/0009* (2013.01); *C07C 6/126* (2013.01); *C07C 2529/40* (2013.01)

(56) References Cited

U.S. PATENT DOCUMENTS

| | | | |
|---|---|---|---|
| 6,559,086 | B1 | 5/2003 | Takahashi et al. |
| 6,867,340 | B2 | 3/2005 | Oh et al. |
| 7,626,064 | B1 * | 12/2009 | Boldingh ................. B01J 29/26 |
| | | | 585/475 |
| 7,663,010 | B2 | 2/2010 | Levin |
| 8,163,966 | B2 | 4/2012 | Levin |
| 8,183,424 | B2 | 5/2012 | Levin et al. |
| 8,481,443 | B2 | 7/2013 | Levin et al. |
| 9,006,125 | B2 | 4/2015 | Levin et al. |
| 9,034,780 | B2 | 5/2015 | Levin |
| 10,053,403 | B2 | 8/2018 | Lai et al. |
| 10,058,853 | B2 | 8/2018 | Lai et al. |
| 10,118,165 | B2 * | 11/2018 | Lai ........................ B01J 29/7461 |
| 10,669,491 | B2 | 6/2020 | McCarthy et al. |
| 11,236,027 | B2 | 2/2022 | Elia et al. |
| 2015/0217281 | A1 | 8/2015 | Berg-Slot et al. |
| 2018/0029025 | A1 | 2/2018 | Elia et al. |
| 2018/0134637 | A1 | 5/2018 | Lai et al. |
| 2019/0359542 | A1 | 11/2019 | Detjen et al. |
| 2022/0126279 | A1 * | 4/2022 | Gatt ........................ B01J 29/44 |

* cited by examiner

CATALYSTS AND PROCESSES FOR CONVERTING AROMATICS

CROSS-REFERENCE TO RELATED APPLICATIONS

This application is a US national phase application of PCT Application Serial No. PCT/US2020/025016 having a filing date of Mar. 26, 2020, which claims priority to and the benefit of U.S. Provisional Application No. 62/826,116 having a filing date of Mar. 29, 2019 and European Patent Application No. 19185107.0 having a filing date of Jul. 9, 2019, the disclosures of all of which are incorporated herein by reference in their entireties.

FIELD

Catalysts and corresponding catalytic methods are provided for conversion of aromatic hydrocarbons to more valuable products, such as transalkylation of heavy aromatics to make xylenes.

BACKGROUND

One source of benzene and xylenes is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains BTX (benzene, toluene, and xylenes), along with ethylbenzene.

Refineries have also focused on the production of benzene and xylenes by transalkylation of lower value $C_{9+}$ aromatics with benzene or toluene to produce xylenes as increasingly important process. Chemical plants would ideally like to process as much of the heavy $C_{9+}$ aromatics as possible while minimizing and potentially removing the toluene/benzene co-feed. Both transalkylation activity and dealkylation activity are important for a successful catalyst system. Transalkylation is the ability to transalkylate methyl groups to form xylenes. Dealkylation activity is the ability to dealkylate ethyl and propyl groups present on the $C_{9+}$ aromatics to allow the formation of lower methyl/ring species that may transalkylate with higher methyl/ring species to form xylenes. Metal function is required to saturate olefins formed during dealkylation while maintaining the integrity of the aromatic saturations. As plants move to increased amounts of $C_{9+}$ in the feed, acceptable activity and catalyst life become challenging.

A catalyst system for the transalkylation of $C_{9+}$ aromatics with $C_6$-$C_7$ aromatics is disclosed in U.S. Pat. No. 7,663,010. The catalyst system described therein comprises (a) a first catalyst comprising a molecular sieve having a Constraint Index in the range of 3-12 (e.g., a 10 MR molecular sieve, such as ZSM-5, ZSM-11, ZSM-22, and ZSM-23) and a metal catalyzing the saturation of the olefins formed by the dealkylation reactions and (b) a second catalyst comprising a molecular sieve having a Constraint Index in the range of less than 3 (e.g., a 12 MR molecular sieve, such as ZSM-12, MOR, zeolite beta, MCM-22 family molecular sieve) and optionally a metal which may be the same or different to the metal on the first catalyst. U.S. Pat. Nos. 8,163,966 and 9,034,780 describe additional catalyst systems and methods for performing transalkylation on mixed aromatic feeds.

U.S. Pat. Nos. 8,183,424, 8,481,443, and 9,006,125 discloses improved performance with a stacked bed system in a process for producing xylene by transalkylation of a $C_{9+}$ aromatic hydrocarbon feedstock contacted with a $C_6$ and/or $C_7$ aromatic hydrocarbon and hydrogen with a first catalyst comprising (i) a first molecular sieve having a Constraint Index in the range of 3 to 12 and (ii) at least first and second different metals or compounds thereof of Groups 6 to 12 of the IUPAC Periodic Table of the Elements under conditions effective to dealkylate aromatic hydrocarbons and to saturate $C_{2+}$ olefins formed so as to produce a first effluent. At least a portion of the first effluent is then contacted with a second catalyst comprising a second molecular sieve having a Constraint Index less than 3 under conditions effective to transalkylate $C_{9+}$ aromatic hydrocarbons with said $C_6/C_7$ aromatic hydrocarbon to form a second effluent comprising xylene.

U.S. Pat. No. 10,118,165 describes catalyst compositions and their use in heavy aromatics conversion processes. The catalyst compositions include a mixture of a first zeolite having a Constraint Index of 3 to 12, a second zeolite corresponding to a mordenite zeolite synthesized from tetraethylammonium cation (TEA) or methyl tetraethylammonium cation (MTEA), a Group 10 metal, and a Group 11-15 metal. Examples of the zeolite including a constraint index of 3 to 12 include ZSM-5 and ZSM-11.

SUMMARY

It has been found, in a surprising manner, that a catalyst composition comprising a mixture of a MEL framework zeolite such as ZSM-11 and a MOR framework zeolite such as mordenite, a metal such as Pt, demonstrated superior performance over similar catalyst compositions free of a MEL framework zeolite, but comprising alternative zeolite such as ZSM-5 in lieu thereof, in terms of one or more of at least aromatic selectivity, ethyl-substituted aromatics, xylene yield, and aging rate in aromatic conversion processes such as transalkylation of $C_{9+}$ aromatics with benzene/toluene.

In a first aspect, this disclosure provides a method for converting a feedstock comprising $C_{8+}$ aromatics, comprising: contacting the feedstock and optionally hydrogen with a catalyst composition under conversion conditions in a reactor comprising at least one fixed catalyst bed of the catalyst composition to produce a converted product mixture, wherein the catalyst composition comprises: (i) a mixture of a first zeolite having a MEL framework and a second zeolite having a MOR framework, having a weight ratio of the first zeolite to the second zeolite ranging from 0.3 to 1.2; and (ii) a combination of a first metal in Group 10 and a second metal in Groups 11 to 15 in the Periodic Table of Elements, having a molar ratio of the second metal to the first metal ranging from 1.0 to 10.

In a second aspect, this disclosure provides a catalyst composition comprising: (i) a mixture of a first zeolite having a MEL framework and a second zeolite having a MOR framework, having a weight ratio of the first zeolite and the second zeolite ranging from 0.3 to 1.2; and (ii) a combination of a first metal in Group 10 and a second metal in Groups 11 to 15 in the Periodic Table of Elements, having a molar ratio of the second metal to the first metal ranging from 1.0 to 10.

DETAILED DESCRIPTION

Overview

In various aspects and embodiments, methods and corresponding catalysts are provided for conversion of an aromatic feed containing $C_{8+}$ aromatics (especially heavy aromatics containing $C_{9+}$ aromatics) to form benzene and/or xylenes. The aromatic feed can be converted in the presence of a catalyst that includes a mixture of a first zeolite having a MEL framework, such as ZSM-11, and a second zeolite having a MOR framework, such as mordenite, particularly mordenite synthesized using TEA or MTEA as a structure directing agent. The weight ratio of the first zeolite to the second zeolite in the catalyst can be from 0.3 to 1.2, or from 0.3 to 1.1, or from 0.3 to 1.0. The catalyst can further include one or more metals supported on the catalyst, such as a combination of metals.

It has been discovered that catalysts including a mixture of a desirable weight ratio of the MEL framework zeolite and the MOR framework zeolite (e.g., mordenite, particularly mordenite synthesized using TEA or MTEA) can provide an unexpectedly beneficial combination of properties. For example, the aromatic selectivity of the catalyst can be unexpectedly high relative to the amount of conversion of ethyl-substituted aromatics. Ethyl-substituted aromatics, such as ethylbenzene, are less desirable components in a product mixture including xylenes, due in part to the difficulty in separating such ethyl-substituted aromatics from other desired products. However, conversion of ethyl-substituted aromatics by saturation and/or opening of the aromatic ring represents a net loss of potential product, as such saturated and/or opened aromatic rings can no longer be recycled easily for production of additional desired aromatic products. Thus, the ability to reduce or minimize aromatic loss (i.e., high aromatic selectivity) while also providing increased amounts of conversion of ethyl-substituted aromatics is beneficial for commercial production of aromatic products, such as benzene, toluene, and/or xylenes.

It has further been discovered that use of a silica binder can unexpectedly reduce or minimize the aging rate of catalyst including a mixture of MEL framework zeolite and mordenite synthesized using TEA or MTEA. This can facilitate the use, for example, of MEL framework zeolite with a lower silica to alumina ratio while providing improved catalyst lifetime.

Figure 1:
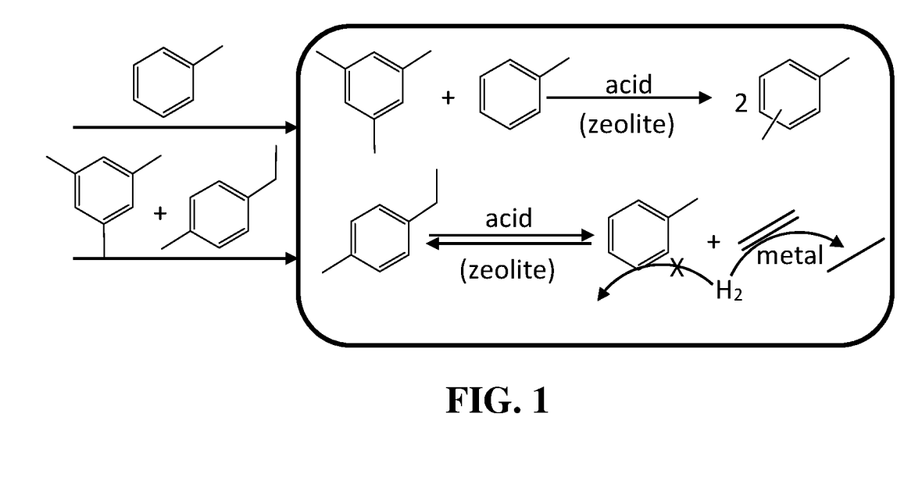
FIG. 1 shows various reaction pathways that can be present during conversion of a heavy aromatic feed.

Conversion of an aromatic feed including $C_{8+}$ (particularly $C_{9+}$) aromatics can require balancing of a variety of reaction mechanisms to achieve a desired product. FIG. 1 shows an overview of several exemplary reactions that can occur during a transalkylation process between toluene and $C_9$ aromatics (represented by 1,3,5-tri-methylbenzene and 1-methyl-4-ethylbenzene, two exemplary $C_9$ aromatic hydrocarbons) in a transalkylation reactor. One desirable reaction is the transalkylation between the $C_9$ aromatic hydrocarbons (e.g., 1,3,5-trimethylbenzene) with toluene to produce highly valuable xylenes catalyzed by an acid such as a zeolite. Another desirable reaction is the de-ethylation of ethyl-containing aromatic hydrocarbons (e.g., 1-methyl-4-ethyl-benzene) to form toluene/benzene and an olefin (e.g., ethylene) in the presence of an acid such as a zeolite. It is highly desirable that the olefin (ethylene) is hydrogenated to ethane in the presence of hydrogenation metal catalyst to prevent it from ethylating an aromatic compound. On the other hand, it would be highly undesirable to allow the aromatics (e.g., toluene) to undergo hydrogenation in the presence of the hydrogenation metal catalyst to form non-aromatic species, resulting in loss of aromatic rings ("ring loss"). The aromatic compounds, including benzene, toluene, xylenes, and the like, are considered high-value molecules than the non-aromatic hydrocarbons. Thus, it would be highly desirable to reduce ring loss and to increase de-ethylation in an aromatic conversion process such as a transalkylation process. The ability to balance the group of reactions shown in FIG. 1 is of high value commercially, as the ability to selectivity remove ethyl-substituted aromatics while reducing or minimizing loss of aromatic rings can allow for increased net yield from conversion of the feed while simplifying the separation processes that are needed to isolate xylenes from other components of the conversion effluent.

Conventionally, some types of catalysts or catalysts systems for conversion of a heavy aromatics effluent can involve using some combination of mordenite, a zeolite such as ZSM-5, and a combination of Pt with another metal supported on the catalyst. For catalysts include mordenite and ZSM-5, use of a combination of Pt with Sn can appear to be less favorable in comparison with a combination of Pt with Ga. This is due in part to lower activity for catalysts including a combination of Pt and Sn for conversion of ethyl-substituted aromatics. However, it has been discovered that when using a combination of ZSM-11 and mordenite synthesized using TEA or MTEA, a combination of Pt and Sn as catalytic metals can provide an unexpectedly beneficial combination of aromatic selectivity (i.e., preserving aromatic rings in the conversion effluent) for a given or target level of conversion of ethyl-substituted aromatics.

As used in this specification, the term "framework type" is used in the sense described in the "Atlas of Zeolite Framework Types," 2001.

The term "aromatic" as used herein is to be understood in accordance with its art-recognized scope which includes alkyl substituted and unsubstituted mono- and polynuclear compounds. The term "ethyl-substituted aromatic" refers to aromatics such as ethylbenzene that include at least one ethyl group as a substituent of the aromatic ring.

The term "hydrocarbon" means (i) any compound consisting of hydrogen and carbon atoms or (ii) any mixture of two or more such compounds in (i). The term "$C_n$ hydrocarbon," where n is a positive integer, means (i) any hydrocarbon compound comprising carbon atom(s) in its molecule at the total number of n, or (ii) any mixture of two or more such hydrocarbon compounds in (i). Thus, a $C_2$ hydrocarbon can be ethane, ethylene, acetylene, or mixtures of at least two of them at any proportion. A "$C_m$ to $C_n$ hydrocarbon" or "$C_m$-$C_n$ hydrocarbon," where m and n are positive integers and m<n, means any of $C_m$, $C_{m+1}$, $C_{m+2}$, . . . , $C_{n-1}$, $C_n$ hydrocarbons, or any mixtures of two or more thereof. Thus, a "$C_2$ to $C_3$ hydrocarbon" or "$C_2$-$C_3$ hydrocarbon" can be any of ethane, ethylene, acetylene, propane, propene, propyne, propadiene, cyclopropane, and any mixtures of two or more thereof at any proportion between and among the components. A "saturated $C_2$-$C_3$ hydrocarbon" can be ethane, propane, cyclopropane, or any mixture thereof of two or more thereof at any proportion. A "$C_{n+}$ hydrocarbon" means (i) any hydrocarbon compound comprising carbon atom(s) in its molecule at the total number of at least n, or (ii) any mixture of two or more such hydrocarbon compounds in (i). A "$C_{n-}$ hydrocarbon" means (i) any hydrocarbon compound comprising carbon atoms in its molecule at the total number of at most n, or (ii) any mixture of two or more such hydrocarbon compounds in (i). A "$C_m$ hydrocarbon stream"

means a hydrocarbon stream consisting essentially of $C_m$ hydrocarbon(s). A "$C_m$-$C_n$ hydrocarbon stream" means a hydrocarbon stream consisting essentially of $C_m$-$C_n$ hydrocarbon(s).

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure. Additionally, they do not exclude impurities and variances normally associated with the elements and materials used. "Consisting essentially of" a component in this disclosure can mean, e.g., comprising, by weight, at least 80 wt %, of the given material, based on the total weight of the composition comprising the component.

In this discussion, references to groups of elements correspond to groups according to the IUPAC Periodic Table. Thus, Group 10 metals include Ni, Pt, and Pd.

As used herein, the term "meso-mordenite" means a mordenite zeolite having a mesopore surface area of greater than 30 $m^2/g$. Said meso-mordenite zeolite can be synthesized from TEA or MTEA, and may comprise agglomerates composed of primary crystallites, wherein said primary crystallites have an average primary crystal size as measured by TEM of less than 80 nm and an aspect ratio of less than 2, as disclosed in U.S. Pat. No. 10,017,394, which is incorporated by reference herein for the limited purpose of describing synthesis of such mordenite zeolite.

As used herein, the term "medium pore zeolite" means a zeolite having a constraint index of 3 to 12. As used herein, the term "constraint index" is defined in U.S. Pat. Nos. 3,972,832 and 4,016,218, both of which are incorporated herein by reference.

As used herein, the term "TEA" means tetraethylammonium cation. As used herein, the term "MTEA" means methyltriethylammonium cation. The term "aspect ratio" when used in reference to the primary crystals is defined as the longest dimension of the crystallite divided by the width of the crystallite, where the width of the crystallite is defined as the dimension of the crystallite in the middle of that longest dimension in a direction orthogonal to that longest dimension, as measured by TEM, is relatively low, for example, less than 2.0. Typically, the primary crystals are not elongated crystals having an aspect ratio greater than 2.0, or platelets.

As used herein, the term "primary crystal" denotes a single, indivisible crystal in contrast to an agglomerate. Primary crystals typically adhere together through weak physical interactions (rather than chemical bonds) to form agglomerates. The words "crystal" and "crystallite" are used herein interchangeably.

Catalyst Composition

The catalyst composition employed in the process of the invention comprises a first zeolite having an MEL framework type, a second zeolite comprising a MOR framework zeolite (e.g., mordenite, particularly mordenite zeolite synthesized from TEA or MTEA), at least one first metal of Group 10, and at least one second metal of Group 11 to 15 of the IUPAC Periodic Table, wherein the MOR framework zeolite can be a meso-porous zeolite having a mesopore surface area of greater than 30 $m^2/g$. The MOR framework zeolite can comprise agglomerates composed of primary crystallites, and wherein the primary crystallites have an average primary crystal size as measured by TEM of less than 80 nm and an aspect ratio of less than 2. Preferably, the Group 10 metal can be Pt and the Group 11 to 15 metal can be Sn. The MOR framework zeolite can be a meso-mordenite.

ZSM-11 is an example of an MEL framework type zeolite. ZSM-11 has a constraint index of 3 to 12. ZSM-11 is described in U.S. Pat. No. 3,709,979, which is incorporated herein by reference. Constraint index and a method for its determination are described in U.S. Pat. No. 4,016,218, which is incorporated herein by reference with regard to the description of constraint index and the method of its determination. Preferably the first zeolite consists essentially of ZSM-11, e.g., comprising ZSM-11 at a concentration of at least, e.g., 85, 90, 95, 98, 99, or even 100 wt %, based on the total weight of the first zeolite.

Another example of MEL framework type zeolite is SSZ-46 (described in U.S. Pat. No. 5,968,474), TS-2 (described in Reddy, J. S. and Kumar, R., Crystallization kinetics of a new titanium silicate with MEL structure (TS-2), *Zeolites,* 12, 95-100 (1992), which can be useful in the first zeolite of the zeolite mixture of the catalyst composition of this disclosure. The contents of these references are incorporated by reference in their entirety. These alternative MEL framework zeolites, and ZSM-11, can be used alone or in combination in or as the first zeolite.

The second zeolite comprises a MOR framework zeolite, such as mordenite, particularly mordenite synthesized from TEA or MTEA structure directing agents. It is desirable that the MOR framework zeolite has a mesopore surface area of greater than 30 $m^2/g$. The MOR framework zeolite can comprise agglomerates of primary crystallites, wherein said primary crystallites have an average primary crystal size as measured by TEM (transmission electron microscopy) of less than 80 nm and an aspect ratio of less than 2. Preferably the second zeolite consists essentially of mordenite, e.g., comprising mordenite at a concentration of at least, e.g., 85, 90, 95, 98, 99, or even 100 wt %, based on the total weight of the second zeolite. Preferably the second zeolite consists essentially of meso-mordenite, e.g., comprising meso-mordenite at a concentration of at least, e.g., 85, 90, 95, 98, 99, or even 100 wt %, based on the total weight of the second zeolite.

Other examples of zeolites having an MOR framework include: RMA1—(described in Itabashi, K., Matsumoto, A., Ikeda, T., Kato, M. and Tsutsumi, K., Synthesis and characteristic properties of Rb-mordenite, *Microporous Mat.,* 101, 57-65 (2007)); Ga—Si—O-MOR, described in Eapen, M. J., Reddy, K. S. N., Joshi, P. N. and Shiralkar, V. P., Synthesis of a Gallosilicate Analogue of High Silica, Large Port Mordenite, *J. Incl. Phenom.,* 14, 119-129 (1992); LZ-211 (described in U.S. Pat. No. 4,503,023); Large-port and small port mordenites described in Sand, L. B., Synthesis of large-port and small-port mordenites, *Molecular Sieves, pp.* 71-77 (1968). The contents of all these references are hereby incorporated by reference in their entirety. These MOR framework type zeolites, together with ZSM-11, maybe used alone or in combination in the second zeolite of the catalyst composition of this disclosure.

The meso-mordenite zeolite can comprise agglomerates, typically irregular agglomerates. The agglomerates are composed of primary crystallites which have an average primary crystal size as measured by TEM of less than 80 nm, preferably less than 70 nm and more preferably less than 60 nm, for example, less than 50 nm. The primary crystallites may have an average primary crystal size as measured by TEM of, for example, greater than 20 nm, optionally greater than 30 nm.

Optionally, the primary crystals of the meso-mordenite zeolite have an average primary crystal size of less than 80 nm, preferably less than 70 nm, and in some cases less than 60 nm, in each of the a, b and c crystal vectors as measured by X-ray diffraction. The primary crystallites may optionally have an average primary crystal size of greater than 20 nm, optionally greater than 30 nm, in each of the a, b and c crystal vectors, as measured by X-ray diffraction.

The meso-mordenite zeolite will generally comprise a mixture of agglomerates of the primary crystals together with some unagglomerated primary crystals. The majority of the meso-mordenite zeolite, for example, greater than 80 weight % or greater than 90 weight % will be present as agglomerates of primary crystals. The agglomerates are typically of irregular form. For more information on agglomerates please see Walter, D. (2013) Primary Particles—Agglomerates—Aggregates, in Nanomaterials (ed. Deutsche Forschungsgemeinschaft (DFG)), Wiley-VCH Verlag GmbH & Co. KGaA, Weinheim, Germany. doi: 10.1002/9783527673919, pages 1-24. Usefully, the meso-mordenite zeolite is not an aggregate.

Optionally, the meso-mordenite zeolite comprises at least 50% by weight, preferably at least 70% by weight, advantageously at least 80% by weight, more preferably at least 90% by weight and optionally substantially consists of said irregular agglomerates composed of primary crystallites having a primary crystal size of less than 80 nm, preferably less than 70 nm, and more preferably less than 60 nm, for example, less than 50 nm Preferably, the meso-mordenite zeolite of the invention comprises less than 10% by weight of primary crystallites having a size of more than 80 nm as assessed by TEM. Preferably, the meso-mordenite zeolite of the invention is composed of said irregular agglomerates composed of crystallites having a crystal size as measured by TEM of less than 80 nm. Preferably, the meso-mordenite zeolite of the invention is substantially free, for example, contains less than 10% by number as assessed by TEM, of needle or platelet crystals.

Preferably, said primary crystallites of the meso-mordenite zeolite of the invention have an aspect ratio of less than 3.0, more preferably less than 2.0, wherein the aspect ratio is defined as the longest dimension of the crystallite divided by the width of the crystallite, where the width of the crystallite is defined as the dimension of the crystallite in the middle of that longest dimension in a direction orthogonal to that longest dimension, as measured by TEM.

Said agglomerates of said primary crystallites are typically of irregular form and may be referred to as being "secondary" particles because they are formed of agglomerates of the crystallites, which are the "primary" particles.

The primary crystallites may have a narrow particle size distribution such that at least 90% of the primary crystallites by number have a primary crystal size in the range of from 20 to 80 nm, preferably in the range of from 20 to 60 nm, as measured by TEM.

The meso-mordenite has a very small crystal size and a high mesopore surface area, in particular by the selection of the synthesis mixture composition. The very small primary crystal size promotes access of reactant compounds to the active sites within the pores of the mordenite, thereby increasing catalytic efficiency.

The meso-mordenite zeolite has a mesopore surface area as measured by BET of greater than 30 m$^2$/g, preferably greater than 40 m$^2$/g, and in some cases greater than 45 m$^2$/g.

The meso-mordenite zeolite preferably has a total surface area of greater than 500 m$^2$/g, more preferably greater than 550 m$^2$/g, and in some cases greater than 600 m$^2$/g. The total surface area includes the surface area of the internal pores (zeolite surface area) and also the surface area on the outside of the crystals (the external surface area). The total surface area is measured by BET.

Preferably, the ratio of the meso-mesopore surface area to the total surface area for the meso-mordenite zeolite is greater than 0.05.

The meso-mordenite zeolite preferably has a mesopore volume of greater than 0.1 mL/g, more preferably greater than 0.12 mL/g, and in some cases greater than 0.15 mL/g.

The Si:Al$_2$ (or SiO$_2$/Al$_2$O$_3$) molar ratio of the meso-mordenite zeolite of the invention is preferably greater than 10 and may be in the range of, for example, from 10 to 60, preferably from 15 to 40. The ratio Si:Al$_2$ of the post-treated mordenite zeolite is preferably in the range of from 40 to 300, more preferably from 60 to 150.

The meso-mordenite zeolite may be prepared by the method comprising the steps of:

a) providing a synthesis mixture comprising a silicon source, an aluminum source, an alkali metal (M) hydroxide, a source of a structure directing agent (SDA) selected from the group consisting of tetraethylammonium cation (TEA), methyltriethylammonium cation (MTEA) and mixtures thereof, optional seed crystals and water, said synthesis mixture having a composition including the following molar ratios:

SiO$_2$:Al$_2$O$_3$ 15-40
OH$^-$:SiO$_2$≤0.32
M$^+$:SiO$_2$≤0.32
SDA:SiO$_2$≤0.10
H$_2$O:SiO$_2$≤20 b) subjecting said synthesis mixture to crystallization conditions to form crystals of a mordenite zeolite comprising the structure directing agent (SDA) within its pores. The components of the synthesis mixture are combined and maintained under crystallization conditions.

Suitable sources of silicon (Si) include silica, colloidal suspensions of silica, precipitated silica, alkali metal silicates such as potassium silicate and sodium silicate, tetraalkyl orthosilicates, and fumed silicas such as Aerosil and Cabosil. Preferably, the source of Si is a precipitated silica such as Ultrasil (available from Evonik Degussa) or HiSil (available from PPG Industries).

Suitable sources of aluminum (Al) include aluminum sulfate, aluminum nitrate, aluminum hydroxide, hydrated alumina such as boehmite, gibbsite and/or pseudoboehmite, sodium aluminate and mixtures thereof. Other aluminum sources include, but are not limited to, other water-soluble aluminum salts, or an aluminum alkoxide, such as aluminum isopropyloxide, or an aluminum metal, such as aluminum in the form of chips. Preferably, the aluminum source is sodium aluminate, for example an aqueous solution of sodium aluminate with a concentration in the range of 40 to 45%, or aluminum sulfate, for example an aluminum sulfate solution with a concentration in the range of from 45 to 50%.

Alternatively or in addition to previously mentioned sources of Si and Al, aluminosilicates may also be used as a source of both Si and Al. Preferably, the SiO$_2$:Al$_2$O$_3$ molar ratio in the synthesis mixture is in the range of from 15 to 40, more preferably from 20 to 30.

The synthesis mixture also contains a source of alkali metal cation M$^+$. The alkali metal cation M$^+$ is preferably selected from the group consisting of sodium, potassium and mixtures of sodium and potassium cations. Sodium cation is preferred. Suitable sodium sources may be, for example, a sodium salt such as NaCl, NaBr or NaNO$_3$, sodium hydroxide or sodium aluminate, preferably sodium hydroxide or sodium aluminate. Suitable potassium sources may be, for example, potassium hydroxide or potassium halide such as KCl or KBr, or potassium nitrate. Preferably, the molar ratio M$^+$:Si in the synthesis mixture is in the range of from 0.15 to 0.32, more preferably from 0.20 to 0.32. Optionally, the molar ratio M$^+$:Si is less than 0.30.

The synthesis mixture also contains a source of hydroxide ions, for example, an alkali metal hydroxide such as sodium hydroxide or potassium hydroxide. Hydroxide can also be present as a counter ion of the structure directing agent or by the use of aluminum hydroxide as a source of Al. Preferably the range OH$^-$:Si is greater than 0.13, and may, for example, be in the range of from 0.15 to 0.32, preferably from 0.20 to 0.32. Optionally, the OH$^-$:Si ratio is less than 0.30. The synthesis mixture optionally comprises seeds. The seeds may be any suitable zeolite seed crystals, such as ZSM-5 or mordenite seed crystals. Preferably, the seeds are mesoporous mordenite crystals. The seeds may, for example, be present in an amount from 0 wt % to 10 wt %, preferably from 0.01 wt % to 10 wt % such as from 0.1 wt % to 5.0 wt % of the synthesis mixture. In a preferred embodiment, the synthesis mixture comprises seeds.

The structure directing agent, also referred to as SDA, is TEA and/or MTEA, preferably TEA, and may be present in any suitable form, for example as a halide, but is preferably present in its hydroxide form. Suitable sources of the structure directing agent include TEABr, TEAOH, MTEACl, MTEABr and MTEAOH. A preferred source of structure directing agent is TEABr. Preferably, the molar ratio SDA:Si is in the range of from 0.005 to 0.10, more preferably from 0.02 to 0.10, especially from 0.02 to 0.05.

The synthesis of small crystal mordenite is favored by having a relatively high solids content in the synthesis mixture. Preferably, the H$_2$O:Si ratio is no more than 20, for example, in the range of from 5 to 20, preferably from 5 to 17, especially from 10 to 17. The synthesis mixture may, for example, have a composition, expressed in terms of molar ratios, as indicated in Table 1 below.

Crystallization can be carried out under either static or stirred conditions in a suitable reactor vessel, such as for example, polypropylene jars or Teflon® lined or stainless steel autoclaves. Suitable crystallization conditions include a temperature of from 100° C. to 200° C., such as 135° C. to 160° C. Preferably, the temperature is less than 145° C. The synthesis mixture may be held at the elevated temperature for a time sufficient for crystallization to occur at the temperature used, for example, from 1 day to 100 days, optionally from 1 to 50 days for example 2 days to 40 days. The synthesis mixture may in some cases be maintained at a first temperature for a first period of from 1 hour to 10 days and then raised to a second, higher temperature for a period of from 1 hour to 40 days. After the crystallization step, the synthesized crystals are separated from the liquid and recovered.

TABLE 1

Meso-Mordenite Synthesis Mixture

| Molar ratio | Preferred | More preferred | Especially preferred |
|---|---|---|---|
| SiO$_2$:Al$_2$O$_3$ | 15 to 40 | 20 to 35 | 20 to 30 |
| OH$^-$:SiO$_2$ | 0.15 to 0.32 | 0.20 to 0.32 | 0.20 to <0.30 |
| M$^+$:SiO$_2$ | 0.15 to 0.32 | 0.20 to 0.32 | 0.20 to <0.30 |
| SDA:SiO$_2$ | 0.005 to 0.10 | 0.02 to 0.10 | 0.02 to 0.05 |
| H$_2$O:SiO$_2$ | 5 to 20 | 5 to 17 | 10 to 17 |

In its as-synthesized form, the second zeolite typically has a chemical composition having the molar relationship shown in Formula (F-1):

$$mQ:nSiO2:Al_2O_3 \qquad (F-1)$$

In Equation (1), m and n are related as 0.001≤m/n≤0.1, for example 0.001≤m/n≤0.05. In Equation (1), n is at least 10, for instance from 10 to 60, preferably from 15 to 40, and Q is the structure directing agent.

Since the as-synthesized meso-mordenite zeolite contains the structure directing agent within its pore structure, the product is usually activated before use in such a manner that the organic part of the structure directing agent, i.e., TEA and/or MTEA, is at least partially removed from the zeolite.

The calcined meso-mordenite zeolite is optionally prepared by calcining the mordenite zeolite to remove the structure directing agent. The meso-mordenite zeolite may also be subjected to an ion-exchange step to replace the alkali or alkaline earth metal ions present in the as-synthesized product with other cations. Preferred replacing cations include metal ions, hydrogen ions, hydrogen precursor such as ammonium ions and mixtures thereof, more preferably hydrogen ions or hydrogen precursors. For instance, the meso-mordenite zeolite may be subjected to an ion-exchange step to replace the alkali or alkaline earth metal ions with ammonium cations, followed by calcination to convert the meso-mordenite zeolite in ammonium form to a meso-mordenite zeolite in hydrogen form. In one embodiment, the meso-mordenite zeolite is first subjected to a calcination step, sometimes referred to as a "pre-calcination" to remove the structure directing agent from the pores of the meso-mordenite zeolite, followed by an ion-exchange treatment, followed by a further calcination step. However, it has been found that for the meso-mordenite zeolite of the present invention, a pre-calcination step is not always required. In an alternative embodiment, the meso-mordenite zeolite is thus subjected to an ion-exchange treatment without being subjected to a prior calcination step (or pre-calcination), and, following the ion exchange treatment, is calcined to remove the structure directing agent from the pores, thereby providing the calcined meso-mordenite zeolite used in the second zeolite of this invention.

The ion-exchange step may involve, for example, contacting the meso-mordenite zeolite with an aqueous ion exchange solution. Such contact may be take place, for example, from 1 to 5 times. The contacting with the ion exchange solution is optionally at ambient temperature, or alternatively may be at an elevated temperature. For example, the meso-mordenite zeolite may be ion exchanged by contact with aqueous ammonium nitrate solution at room temperature followed by drying and calcination.

Suitable calcination conditions include heating at a temperature of at least 300° C., preferably at least 370° C. for at least 1 minute and generally not longer than 20 hours, for example, for a period of from 1 hour to 12 hours. While subatmospheric pressure can be employed for the thermal treatment, atmospheric pressure is desired for reasons of convenience. The thermal treatment can be performed at a temperature up to 925° C. For instance, the thermal treatment can be conducted at a temperature of from 400° C. to 600° C., for instance from 500° C. to 550° C., in the presence of an oxygen-containing gas.

The calcined meso-mordenite zeolite typically has a Si:Al$_2$ ratio of at least 10, for example 10 to 60, more preferably 15 to 40.

The catalyst composition of this invention comprises a first zeolite corresponding to a MEL framework type zeolite having a constraint index of 3 to 12, such as ZSM-11; a second zeolite comprising a meso-mordenite zeolite; at least one first metal of Group 10 of the IUPAC Periodic Table, such as Pt; and at least one second metal of Group 11 to 15 of the IUPAC Periodic Table, such as Sn. In some embodiments, the weight ratio of the first zeolite to the second zeolite in the catalyst can be any convenient ratio, such as having 1 wt % to 99 wt % of the first zeolite, or 10 wt % to 80 wt %, and/or 1 wt % to 99 wt % of the second zeolite, or 10 wt % to 80 wt %. In some embodiments, the weight ratio of the first zeolite to the second zeolite can be 0.3 to 1.2, or 0.3 to 1.1, or 0.3 to 1.0. The first zeolite and second zeolite can be present as a mixture that is formed in any convenient manner. For example, the zeolites can be co-extruded into particles, or the zeolites can be separately extruded into particles and then mixed in a catalyst bed.

In addition to the first zeolite and the second zeolite, the catalyst comprises at least one first metal of Group 10 of the IUPAC Periodic Table, and at least one second metal of Group 11 to Group 15 of the IUPAC Periodic Table. The first metal of Group 10 metal includes, but is not limited to, one or more of nickel (Ni), palladium (Pd), platinum (Pt), and compounds containing natural metals or ions thereof, preferably platinum. The second metal of Group 11 to Group 15 includes, but is not limited to, one or more of copper (Cu), silver (Ag), gold (Au), zinc (Zn), cadmium (Cd), gallium (Ga), indium (In), tin (Sn), bismuth (Bi), and compounds containing natural metals or ions thereof, preferably tin.

In some embodiments, the catalyst composition can include 0.001 wt % to 5.0 wt % of Pt, or 0.01 wt % to 1.0 wt %, or 0.05 wt % to 0.6 wt %. For example, the catalyst composition can include 0.005 wt % or more of Pt, or 0.01 wt % or more, or 0.05 wt % or more, or 0.10 wt % or more, such as up to 2.0 wt %, or up to 5.0 wt %, based on the weight of the catalyst composition. Additionally or alternately, in such embodiments, the catalyst composition can include 0.005 wt % to 5.0 wt % Sn, or 0.05 wt % to 2.0 wt %. For example, the catalyst composition can include 0.005 wt % or more of Sn, or 0.01 wt % or more, or 0.05 wt % or more, or 0.10 wt % or more, such as up to 2.0 wt %, or up to 5.0 wt %, based on the weight of the catalyst composition. Optionally but preferably, the catalyst composition can include a molar ratio of Sn to Pt of 0.5 to 10, or 1.0 to 10, or 0.5 to 7.0, or 1.0 to 7.0.

The metal component, for example, the first metal and/or the second metal, may be provided on the catalyst composition in any manner, for example, by conventional methods such as impregnation or ion exchange of the first zeolite and/or the second zeolite with a solution of a compound of the relevant metal before or after forming the catalyst particle.

It may be desirable to incorporate another material into the first zeolite and the second zeolite in the catalyst composition that is resistant to the temperatures and other conditions employed in the transalkylation process of the invention. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

The catalyst can further include at least one binder. Non-limiting examples of binders useful in the catalyst composition of this disclosure are: alumina, silica, clay, titania, zirconia, kaolin, clay, and a mixture of two or more thereof, and the like. Use of a material in conjunction with the first zeolite and the second zeolite, i.e. combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, naturally occurring clays, for example bentonite and kaolin, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with the first zeolite and the second zeolite as a binder for the catalyst composition include the montmorillonite and kaolin family, which families include the subbentonites, and the kaolins commonly known as Dixie, McNamee, Ga. and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the first zeolite and the second zeolite may be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form to facilitate extrusion of the catalyst composition.

Each zeolite is usually admixed with the binder or matrix material so that the final catalyst composition contains the binder or matrix material in an amount ranging from 5 to 90 wt %, and typically from 10 to 60 wt %, based on the weight of the catalyst composition. For example, the binder can correspond to 5 wt % to 50 wt % of the catalyst composition, or 5 wt % to 30 wt %, or 10 wt % to 30 wt %.

Prior to use, steam treatment of the catalyst composition may be employed to minimize the aromatic hydrogenation activity of the catalyst composition. In the steaming process, the catalyst composition is usually contacted with from 5% to 100% steam, at a temperature of at least 260° C. to 650° C. for at least one hour, specifically 1 to 20 hours, at a pressure of 100 to 2590 kPA-a and a WHSV of 0.002 $hr^{-1}$ to 20 $hr^{-1}$.

In addition, prior to contacting the catalyst composition with the hydrocarbon feed, the hydrogenation component can be sulfided. This is conveniently accomplished by contacting the catalyst with a source of sulfur, such as hydrogen sulfide, at a temperature ranging from 320° C. to 480° C. The source of sulfur can be contacted with the catalyst via a carrier gas, such as hydrogen or nitrogen.

After contacting the catalyst composition with the hydrocarbon feed, the catalyst may be deactivated due to coking or metal agglomerization. The deactivated catalyst can be regenerated conveniently by coke burning with a stream comprising oxygen or oxygen containing compounds, such as, ozone, oxochlorine, carbon dioxide or the like, metal re-dispersing using oxdization-reduction cycle, oxochloride treatment or the like, washing with liquid hydrocarbons or aqueous solution of inorganic and/or organic chemical compounds, such as, water, ethanol, acetone, or the like, or rejuvenation with a stream comprising hydrogen. Regeneration or rejuvenation can be performed at a temperature range from ambience to 600° C., a pressure range of 100 kPa-a to 5000 kPa-a, and WHSV of 0.2 hr$^{-1}$ to 100 hr$^{-1}$.

Feedstock

The feedstock used in the process of the invention comprises one or more aromatic compounds containing at least 8 carbon atoms, for example, $C_8$ aromatic hydrocarbons. Specific $C_8$ aromatic hydrocarbons include ethylbenzene and dimethylbenzene isomers. Typically, such $C_{8+}$ aromatic hydrocarbons comprise aromatic compounds having a boiling point in the range of 135 to 230° C. at atmospheric pressure.

In some embodiments, the feedstock can include aromatic compounds having 9 or more carbon atoms, for example, $C_{9+}$ aromatic hydrocarbons. Specific $C_{9+}$ aromatic compounds found in a typical feed can include mesitylene (1,3,5-trimethylbenzene), durene (1,2,4,5-tetramethylbenzene), hemimellitene (1,2,4-trimethylbenzene), pseudocumene (1,2,4-trimethylbenzene), ethyltoluene, ethylxylene, 1,2-methylethylbenzene, 1,3-methylethylbenzene, 1,4-methylethylbenzene, propyl-substituted benzenes, butyl-substituted benzenes, dimethylethylbenzenes, methylpropylbenzene, methylbutylbenzene, and a mixture of two or more thereof.

Suitable sources of the $C_{9+}$ aromatics are any $C_{9+}$ fractions from any refinery process that is rich in aromatics. In some embodiments, the aromatics fraction can include a substantial proportion of $C_{9+}$ aromatics, for example, at least 80 wt % $C_{9+}$ aromatics, wherein preferably at least 80 wt %, and more preferably more than 90 wt %, of the hydrocarbons will range from $C_9$ to $C_{12}$. Typical refinery fractions which may be useful include catalytic reformate, fluidized catalytic cracking (FCC) naphtha or thermoform catalytic cracking (TCC) naphtha.

The feedstock may also comprise benzene or toluene or a mixture of benzene and toluene. Thus, in one practical embodiment, the feed to a transalkylation reactor in a transalkylation process can comprise ethylbenzene, $C_{9+}$ aromatics hydrocarbons and toluene. The feedstock may also include recycled/unreacted/produced benzene, toluene, ethylbenzene, and $C_{9+}$ aromatics that is obtained by distillation of the effluent product of the transalkylation reaction itself. Typically, toluene constitutes from 5 wt % to 90 wt % and $C_{9+}$ constitutes from 10 to 95 wt % of the feedstock. In a typical light feedstock, toluene constitutes from 40 wt % to 90 wt %, such as from 50 wt % to 70 wt % of the entire feed, whereas the $C_{9+}$ aromatics component constitutes from 10 to 60 wt %, such as from 30 to 50 wt %, of the entire feedstock to the transalkylation reaction zone. In a typical heavy feed, toluene constitutes from 15 wt % to 50 wt %, such as from 25 to 40 wt % of the entire feed, whereas the $C_{9+}$ aromatics component constitutes from 50 to 85 wt %, such as from 60 to 75 wt %, of the entire feed to the transalkylation reaction zone.

Hydrocarbon Conversion Process

The process for the conversion of a feedstock comprising $C_{8+}$ aromatic hydrocarbons to converted product mixture comprises the steps of contacting said feedstock and optionally hydrogen in the presence of any one of the catalyst compositions of this invention under suitable conversion conditions to produce said converted product mixture comprising, e.g., benzene, toluene and xylene.

The process can be conducted in any appropriate reactor including a radial flow, fixed bed, continuous flow or fluid bed reactor. In one alternative, the reactor for contacting said feedstock under said suitable conversion conditions comprises at least one single fixed catalyst bed of said catalyst. In another alternative, the reactor for contacting said feedstock under said suitable conversion comprises at least one moving catalyst bed of said catalyst.

The conversion conditions typically include a temperature ranging from 340° C. to 515° C., such as from 400° C. to 454° C.; a pressure from 380 to kPa-a 4240 kPa-a, such as from 1480 kPa-a to 3550 kPa-a; a hydrogen to hydrocarbon molar ratio from 1 to 5, such as from 1 to 3 and a WHSV of 0.2 hr$^{-1}$ to 100 hr$^{-1}$, such as from 1 hr$^{-1}$ to 100 hr$^{-1}$. The transalkylation reaction conditions are sufficient to convert the heavy aromatics-containing feed to a product containing substantial quantities of $C_6$-$C_8$ aromatic compounds, such as benzene, toluene and xylenes, especially benzene and xylene. The transalkylation reaction conditions also are sufficient to convert the ethylbenzene in the feed to benzene and ethane.

In one preferred embodiment, contacting the feedstock with the catalyst composition is effected in the presence of hydrogen fed into the reactor. The presence of hydrogen is particularly advantageous where in the conversion process, dealkylation of certain alkyl benzenes occurs to produce an olefin. It is desirable that such olefin is saturated by the hydrogen present in the reaction in a hydrogenation reaction catalyzed by the catalyst composition of this disclosure.

In a particularly advantageous embodiment of the conversion process of this disclosure, $C_{9+}$ hydrocarbons in the feed react with benzene and/or toluene in the feed in the presence of the catalyst composition to produce a converted product mixture rich in xylenes, which can be separated to produce valuable products such as para-xylene and/or ortho-xylene.

In this disclosure, a "feed" or "feedstock" is used to mean the aggregate of all materials fed into a reactor or a vessel. It should be understood to mean feeding one or multiple streams of materials into the reactor or vessel, with the same or different compositions.

EXAMPLES

The measurement of average primary particle size and primary particle size distribution was carried out as follows. Several TEM photographs of the zeolite sample were taken; primary particles were identified and measured. For each primary particle having an aspect ratio greater than 1, the longest dimension was identified by drawing a line between the two points at the edge of the particle which were the furthest apart. Then the length of the primary particle along a 450 diagonal to that longest dimension and passing through the mid-point of that longest dimension was measured as the particle size. Each measurement was grouped by being assigned to one of 10 particle size ranges covering the range of sizes found in the sample. For example, size ranges centered around 187.5, 250, 312.5, 375, 437.5, 500, 562.5 and 625 Angstroms could be used. The percent (%) crystals value on the y-axis was calculated from: Number of particles in each group/total number of particles measured multiplied by 100. The average particle size was calculated as the arithmetical mean based on the grouped results.

The total BET and the t-Plot micropore surface area were measured by nitrogen adsorption/desorption with a Micromeritics Tristar II 3020 instrument after degassing of the calcined zeolite powders for 4 hrs at 350° C. The mesopore surface area was obtained by the subtraction of the t-plot micropore from the total BET surface area. The mesopore volume was derived from the same data set. More information regarding the method can be found, for example, in "Characterization of Porous Solids and Powders: Surface Area, Pore Size and Density", S. Lowell et al., Springer, 2004.

The X-ray diffraction data (powder XRD or XRD) were collected with a Bruker D4 Endeavor diffraction system with a VÅNTEC multichannel detector using copper K-alpha radiation. The diffraction data were recorded by scanning mode with 0.018 degrees two-theta, where theta is the Bragg angle, and using an effective counting time of 30 seconds for each step.

The crystal sizes in the a, b and c crystal vectors were calculated based on the three (200), (020) and (002) peaks in the X-ray diffraction patterns using the Scherrer equation (P. Scherrer, N. G. W. Gottingen, Math-Pys., 2, p. 96-100 (1918)). The method and its application to zeolites are also described in A. W. Burton, K. Ong, T. Rea, I. Y. Chan, Microporous and Mesoporous Materials, 117, p. 75-90 (2009). For the measurements described herein the Jade version 9.5.1 X-ray diffraction analysis software by Materials Data, Inc., was used to perform the calculation.

The Alpha value is a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Example 1—Preparation of Meso-Mordenite Crystals

A mixture was prepared from using water, TEABr (50% solution), Ultrasil silica, sodium aluminate solution (45%), and 50% sodium hydroxide solution. Mordenite seeds were then added to the mixture. The mixture had the following molar composition:

$SiO_2/Al_2O_3$~26.10
$H_2O/SiO_2$~15.11
$OH^-/SiO_2$~0.291
$Na^+/SiO_2$~0.291
Template/$SiO_2$~0.049

The mixture was reacted at 290° F. (145° C.) with stirring at 350 RPM for 72 hours. The product was filtered, washed with deionized (DI) water and dried at 250° F. (120° C.). The XRD pattern of the as-synthesized material showed the typical pure phase of mordenite topology. The SEM of the as-synthesized material showed morphology of irregularly-shaped aggregates composed of small crystallites. The as-synthesized crystals were pre-calcined in nitrogen at 540° C. and then converted into the hydrogen form by three ion exchanges with ammonium nitrate solution at room temperature, followed by drying at 250° F. (120° C.) and calcination at 1000° F. (540° C.) for 6 hours. The resulting mordenite crystals had a $SiO_2/Al_2O_3$ molar ratio of ~21, surface area of 637 $m^2/g$ and meso-pore surface area of 56 $m^2/g$, Hexane sorption of 53.3 mg/g and an Alpha value of 1200.

Examples 2 to 4: Synthesis of ZSM-11 Crystals

Mixtures were prepared from water, TBABr (50% solution), Ultrasil™ silica, aluminum sulfate solution (47%), 50% sodium hydroxide solution, and ZSM-11 seeds. The compositions of the three types of synthesis mixtures are shown in Table 2. Table 2 also shows the initial mixing and stirring conditions.

TABLE 2

ZSM-11 Synthesis Mixtures

| | Example 2 | Example 3 | Example 4 |
|---|---|---|---|
| Si/Al$_2$ molar ratio in crystal | ~45:1 | ~90:1 | ~27:1 |
| Molar ratios in synthesis mixture for making crystal | SiO$_2$/Al$_2$O$_3$ ~50.2<br>H$_2$O/SiO$_2$ ~13.9<br>OH$^-$/SiO$_2$ ~0.15<br>Na$^+$/SiO$_2$ ~0.26<br>Template/SiO$_2$ ~0.06 | SiO$_2$/Al$_2$O$_3$ ~100<br>H$_2$O/SiO$_2$ ~18.4<br>OH$^-$/SiO$_2$ ~0.14<br>Na$^+$/SiO$_2$ ~0.19<br>Template/SiO$_2$ ~0.05 | SiO$_2$/Al$_2$O$_3$ ~28.3<br>H$_2$O/SiO$_2$ ~13.6<br>OH/SiO$_2$ ~0.10<br>Na$^+$/SiO$_2$ ~0.31<br>Template/SiO$_2$ ~0.08 |
| Reaction conditions for making crystal | Reacted at 121° C./350 RPM for 72 hours, then 138° C./350 rpm for 48 hrs | Reacted at 143° C./250 RPM for 48 hours | Reacted at 121° C./250 RPM for 48 hours, then 138° C./250 RPM for 24 hours |

The products were then filtered, washed with deionized (DI) water, and dried at 250° F. (120° C.). The XRD patterns for each of the resulting crystals (i.e., the as-synthesized material) showed the typical pure phase of ZSM-11 topology. The SEM of the as-synthesized material showed morphology of agglomerates composed of small crystallites with size of <0.05 micron. The as-synthesized crystals were converted into the hydrogen form by three ion exchanges with ammonium nitrate solution at room temperature, followed by drying at 250° F. (120° C.) and calcination at 1000° F. (540° C.) for 6 hours. The crystals from Example 2 had a total surface area (SA) (i.e., micropore SA+mesopore SA) of 481 $m^2/g$, and a hexane sorption of 96.9 mg/g. The crystals from Example 4 had a total surface area (SA) (i.e., micropore SA+mesopore SA) of 484 $m^2/g$, and a hexane sorption of 98.2 mg/g.

Example 5 (Comparative)—Synthesis of ZSM-5 Crystals

A mixture was prepared from water, TPABr (35% solution), HiSil™ silica, 45% Sodium aluminate solution, 50% sodium hydroxide solution, and ZSM-5 seeds. The mixture had the following molar composition:

$SiO_2/Al_2O_3$~61
$H_2O/SiO_2$~11
$OH^-/SiO_2$~0.18
$Na^+/SiO_2$~0.18
Template/$SiO_2$~0.05

The mixture was reacted at temperatures from 100° C. to 150° C. with stirring. The product was filtered, washed with deionized (DI) water and dried at 250° F. (120° C.). The XRD pattern of the as-synthesized material showed the typical pure phase of ZSM-5 topology. The SEM of the as-synthesized material showed morphology of agglomerates composed of small crystallites with size of <0.1 micron. The as-synthesized crystals were pre-calcined in nitrogen at 540° C. and then converted into the hydrogen form by three ion exchanges with ammonium nitrate solution at room temperature, followed by drying at 250° F. (120° C.) and calcination at 1000° F. (540° C.) for 6 hours. The resulting ZSM-5 crystals had a $SiO_2/Al_2O_3$ molar ratio of ~50, a total surface area (SA) of 480 $m^2/g$, and a hexane sorption of ~100 mg/g.

Example 6 (Comparative)—0.30 wt % Pt/3×Ga on 50 wt % Meso-Mordenite/20 wt % ZSM-5/30 wt % Alumina 50 parts of meso-mordenite crystals from Example #1 were mixed with 20 parts of ZSM-5 crystals from example 5 and 30 parts alumina (Versal 300) in a muller. An aqueous solution of Tetraammineplatinum chloride and Gallium (III) Nitrate in water was added to the muller prior to forming to a target loading on the final extrudates of 0.03 wt % Pt and 0.032 wt % Ga. Sufficient water was added to produce an extrudable paste on an extruder, ranging from 49-53% total solids. The mixture was extruded into ¹⁄₁₆" cylinder and then dried on a conveyor convection oven at 121° C. for several hours. The dried extrudates was precalcined in nitrogen at 538° C. to decompose and remove the organic template. The precalcined extrudates were then humidified with saturated air at ambient conditions for an hour at 2 cc/g/min. After humidification, the extrudates were exchanged with 1 N ammonium nitrate to remove sodium. The extrudates were then washed with deionized water to remove residual nitrate ions prior to drying at 121° C. for at least 4 hours, followed by calcination in air at 538° C.

Examples 7-31: Preparation of Meso-Mordenite/ZSM-11/Binder

A series of catalysts including meso-mordenite, ZSM-11, alumina binder, Pt, and Sn were prepared using the following procedure. The amounts of each component in the resulting catalyst are shown in Table 3 below. The relative molar amount of Sn versus Pt is also shown.

Meso-mordenite crystals from Example 1 were mixed with ZSM-11 crystals and alumina (as a binder) in a muller. Most of the mixtures included the ZSM-11 crystals from Example 2. The exceptions are Examples 22 and 23 (ZSM-11 according to Example 3, indicated by ) and Examples 24 and 25 (ZSM-11 according to Example 4, indicated by *). The binder is alumina (Versal 300), unless it is noted that silica was used as the binder (Examples 23, 25, and 30). An aqueous solution of Tetraammineplatinum chloride and Tin(II) chloride dehydrate was added to the muller to a desired target loading prior to forming the final extrudates of Pt and Sn. Sufficient water was added to produce an extrudable paste on a 1" extruder, ranging from 49-53% total solids. The mixture of meso-mordenite (Example 1), ZSM-11, alumina, and water was extruded into ¹⁄₁₆" cylinder and then dried in a hotpack oven at 121° C. overnight. The dried extrudates were precalcined in nitrogen at 538° C. to decompose and remove the organic template. The precalcined extrudates were then humidified with saturated air at ambient conditions for an hour at 2 cc/g/min. After humidification, the extrudates were exchanged with 1 N ammonium nitrate to remove sodium. The extrudates were then washed with deionized water to remove residual nitrate ions prior to drying at 121° C. for at least 4 hours, followed by calcining in air at 538° C.

TABLE 3

Compositions for Examples 7-31

| Example No. | Meso-Mordenite (wt %) | ZSM-11 (wt %) | Binder (wt %) | Pt (wt %) | Sn (wt %) | Sn/Pt molar ratio |
|---|---|---|---|---|---|---|
| 7 | 44 | 36 | 20 | 0.03 | 0.11 | 6 |
| 8 | 50 | 20 | 30 | 0.026 | 0.096 | 6 |
| 9 | 30 | 10 | 60 | 0.03 | 0.11 | 6 |
| 10 | 50 | 20 | 30 | 0.03 | 0.11 | 6 |
| 11 | 64 | 16 | 20 | 0.03 | 0.016 | 1 |
| 12 | 26 | 26 | 48 | 0.03 | 0.016 | 1 |
| 13 | 64 | 16 | 20 | 0.015 | 0.055 | 6 |
| 14 | 26 | 26 | 48 | 0.015 | 0.055 | 6 |
| 15 | 42 | 38 | 20 | 0.015 | 0.091 | 10 |
| 16 | 44 | 37 | 20 | 0.015 | 0.009 | 1 |
| 17 | 30 | 10 | 60 | 0.015 | 0.091 | 10 |
| 18 | 30 | 10 | 60 | 0.015 | 0.009 | 1 |
| 19 | 64 | 16 | 20 | 0.03 | 0.183 | 10 |
| 20 | 26 | 26 | 48 | 0.03 | 0.183 | 10 |
| 21 | 40 | 16 | 44 | 0.03 | 0.164 | 9 |
| 22 | 50 | 20** | 30 | 0.026 | 0.095 | 6 |
| 23 | 50 | 20** | 30 (Silica) | 0.026 | 0.095 | 6 |
| 24 | 50 | 20*** | 30 | 0.026 | 0.095 | 6 |
| 25 | 50 | 20*** | 30 (Silica) | 0.026 | 0.095 | 6 |
| 26 | 50 | 20 | 30 | 0.026 | 0.048 | 3 |
| 27 | 50 | 20 | 30 | 0.026 | 0.145 | 9 |
| 28 | 50 | 20 | 30 | 0.026 | 0.193 | 12 |
| 29 | 40 | 16 | 44 | 0.021 | 0.077 | 6 |
| 30 | 40 | 16 | 44 (Silica) | 0.021 | 0.077 | 6 |
| 31 | 30 | 12 | 58 | 0.016 | 0.058 | 6 |

Example 32—Aromatic Conversion Results

The catalysts in Examples 7-31 were tested in a laboratory scale fixed bed unit using a feed corresponding to 60 wt % of a $C_{9+}$ raffinate and 40 wt % toluene. For each example, the extrudate was sized to 14-18 mesh (1000-1410 μm) and loaded into the reactor with equal parts quartz. The catalysts were activated by heating in hydrogen to 400° C. and held at that temperature for 2 hours. The catalysts were then cooled to 350° C., and then the feed blend was introduced.

The catalyst was contacted with the feedstock at a temperature of 350° C., a pressure of 390 psig (~2.7 MPa-g), and a weight hourly space velocity of 3.0 $hr^{-1}$ to generate results. Temperature excursions to temperatures of as high as 400° C. were periodically used in the presence of the feed in order to simulate catalyst aging.

Table 4 below shows results from various catalysts, as indicated by the Example number.

The results in Table 4 include aromatic selectivity in the conversion effluent, $C_{9+}$ conversion, and xylene yield. Aging rates for the catalyst activity for both $C_{9+}$ conversion and xylene yield are also provided. For the results in Table 4, the results are reported as index or normalized values in comparison with the results obtained for Comparative Example 6. Thus, the aromatic selectivity, $C_{9+}$ conversion, xylene yield, and the aging rates for Comparative Example 6 are normalized to either 1.0 or 0 (for the aging rates). It is noted that for the aging rates, a negative value represents less aging of the catalyst, so that a negative value means the catalyst is retaining more of the indicated activity over time.

TABLE 4

Aromatic Selectivity, $C_{9+}$ Conversion, and Xylene Yields

| Example No. | Relative Aromatic Selectivity | Relative $C_{9+}$ Conversion | Relative $C_{9+}$ Conversion Aging Rate | Relative Xylene Yield | Relative Xylene Yield Aging Rate |
|---|---|---|---|---|---|
| 6 (Comparative) | 1.0 | 1.0 | +0.0 | 1.0 | +0.0 |
| 7 | 1.004 | 1.19 | −52.5% | 1.09 | −52.2% |
| 8 | 1.004 | 1.03 | −31.1% | 1.04 | −41.3% |
| 11 | 0.99 | 1.2 | −54.1% | 1.13 | −50% |
| 13 | 1.013 | 1.06 | −39.3% | 1.08 | −34.8% |
| 15 | 1.015 | 1.14 | −26.2% | 1.06 | −23.9% |
| 19 | 0.99 | 1.20 | −62.3% | 1.13 | −76.1% |
| 24 | 1.014 | 1 | −16.4% | 1.03 | −15.2% |
| 25 | 1.014 | 1.02 | −63.9% | 1.03 | −60.1% |
| 28 | 1.005 | 0.96 | −14.8% | 1.0 | +6.5% |

Table 4 demonstrates a variety of results. First, with the exception of Example 28, the various combinations of meso-mordenite and ZSM-11 with various ratios of Pt and Sn appear to provide substantial catalyst lifetime advantages while providing similar or better aromatic selectivity, $C_{9+}$ conversion, and xylene yield. Example 28 is notable for having an increased ratio of Sn to Pt (molar ratio of 12). Thus, molar ratios of Sn to Pt of 1.0 to 10 are preferable for providing improved resistance to aging while also providing desirable activity.

Another result demonstrated by Table 4 is that reducing the metal content of the catalyst appears to provide for improved aromatic selectivity, as shown in Examples 13 and 15.

Still another result in Table 4 can be observed in Examples 7, 11, 19, and 25. These examples represent the largest decrease in catalyst aging rate relative to the baseline catalyst from Example 6. It is noted that Examples 7, 11, and 19 correspond to catalysts with a 4:1 weight ratio of meso-mordenite to ZSM-11. However, Example 25 corresponds to only a 2.5:1 weight ratio of meso-mordenite to ZSM-11. Example 25 also corresponds to a catalyst that includes a silica binder rather than an alumina binder. Thus, use of a silica binder provides an unexpected improvement in catalyst lifetime for catalysts corresponding to mixtures of meso-mordenite and ZSM-11. It is noted that Example 24 has the same zeolite and metal content, but with an alumina binder. The selectivity, $C_{9+}$ conversion, and xylene yields are similar for Examples 24 and 25, but Example 25 provides an unexpectedly superior aging rate.

Figure 2:
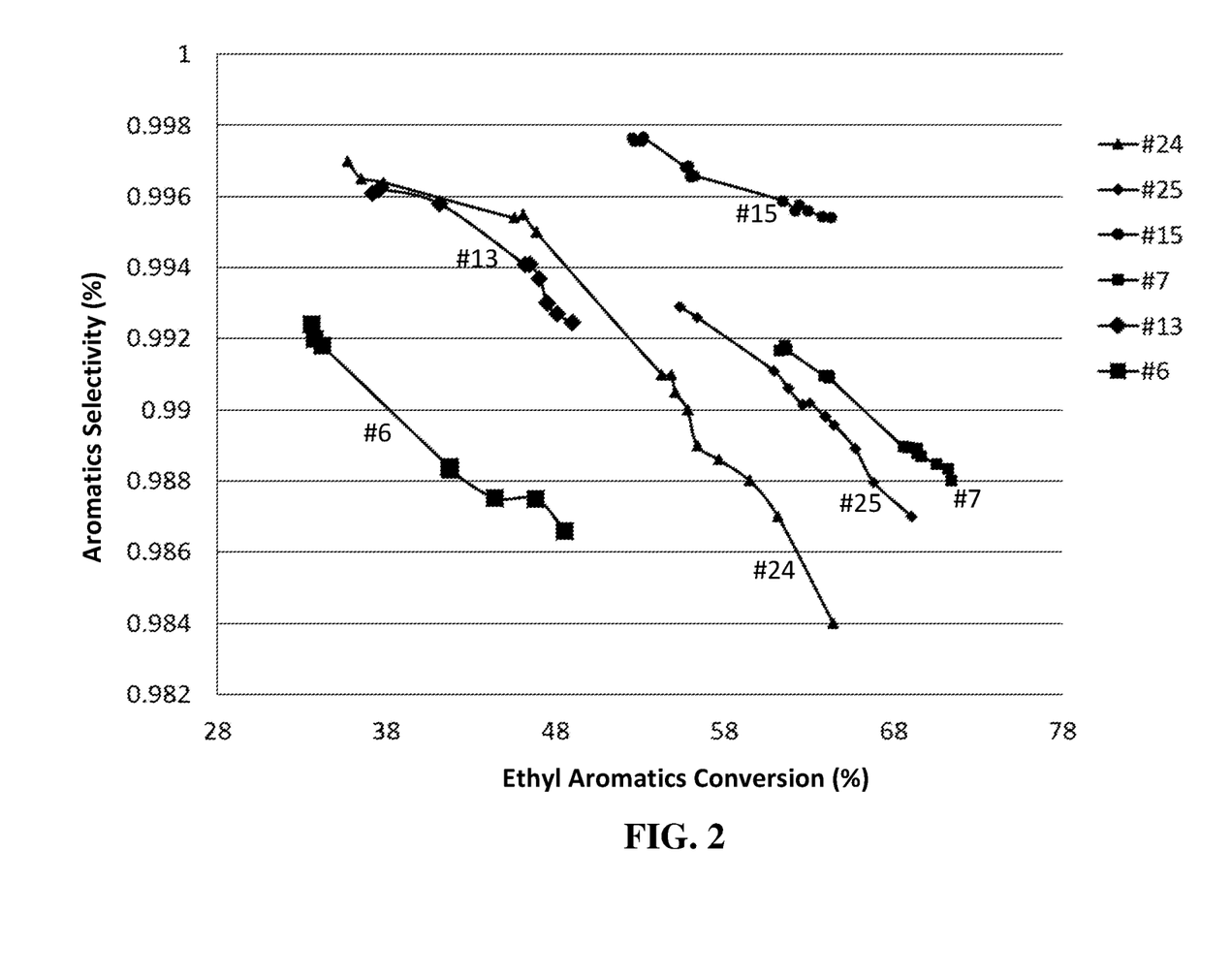
FIG. 2 shows aromatic selectivity relative to ethyl aromatics conversion for various catalysts.

Although Table 4 shows that increased ratios of meso-mordenite to ZSM-11 result in decreased catalyst aging, it has been unexpectedly discovered that decreasing the weight ratio of meso-mordenite to ZSM-11 can provide an enhancement to aromatic selectivity relative to the amount of conversion of ethyl-substituted aromatics. FIG. 2 shows aromatic selectivity versus conversion of ethyl-substituted aromatics for various catalysts from Table 4. In FIG. 2, trend lines toward the upper right corner of the figure correspond to trend lines for catalysts with favorable combinations of aromatic selectivity and conversion of ethyl-substituted aromatics. As shown in FIG. 2, the most favorable combinations of aromatic selectivity versus conversion of ethyl-containing aromatics are provided by Examples 7 and 15, which correspond to roughly 1:1 ratios of meso-mordenite to ZSM-11 (46:34 and 42:38, respectively). It appears that still further benefit is provided by the lower metals content in Example 15. By contrast, the worst performance for aromatic selectivity versus conversion of ethyl-containing aromatics is provided by Example 13, which corresponds to a 64:16 ratio of meso-mordenite to ZSM-11. More generally, weight ratios of meso-mordenite to ZSM-11 of 3.0 or less, or 2.5 or less, can provide unexpected improvements in the ratio of aromatic selectivity to conversion of ethyl-substituted aromatics.

It is noted that one of the conventional difficulties with Pt/Sn supported on meso-mordenite and ZSM-11 is that the conversion of ethyl-substituted aromatics can be relatively low in comparison with the conversion temperature. The results shown in FIG. 2 demonstrate that although the activity for conversion of ethyl-substituted aromatics may be low relative to a conversion temperature, the resulting combination of aromatic saturation and conversion of the ethyl-substituted aromatics is unexpectedly beneficial.

In addition to the above, it is noted that all of the catalysts corresponding to meso-mordenite/ZSM-11 with supported Pt/Sn had superior combinations of aromatic selectivity and conversion of ethyl-substituted aromatics relative to Comparative Example 6 (meso-mordenite/ZSM-5 with supported Pt/Ga).

Example 33—Additional Activity Trends

Still other trends can be determined from the various examples by comparing examples where one feature is varied with others remaining constant. This data is shown in Table 5. For the data in Table 5, the aromatic selectivity, $C_{9+}$ conversion, and xylene yield are shown both at the initial value and after two weeks of catalyst aging.

TABLE 5

Activity Trends

| Example No. | Aromatic Selectivity | Aged Aromatic Selectivity | C$_{9+}$ Conversion | Aged C$_{9+}$ Conversion | Xylene Yield | Aged Xylene Yield |
|---|---|---|---|---|---|---|
| 11 | 96.41 | 97.54 | 56.58 | 50.89 | 35.8 | 31.22 |
| 12 | 86.85 | 90.79 | 52.97 | 39.64 | 31.07 | 21.31 |
| 7 | 97.97 | 98.35 | 56.22 | 50.45 | 34.79 | 30.28 |
| 13 | 98.83 | 99.19 | 50.18 | 42.68 | 34.36 | 28.37 |
| 14 | 97.18 | 98.25 | 46.71 | 34.62 | 30.7 | 22.76 |
| 9 | 94.54 | 96.21 | 50.34 | 40.09 | 33.27 | 26.08 |
| 8 | 96.81 | 97.66 | 57.24 | 52.54 | 35.83 | 32.7 |

Table 5 includes two different comparisons where the weight ratio of meso-mordenite to ZSM-11 is varied, but the remaining variables are kept the same. Example 11 corresponds to a 64:16 ratio of meso-mordenite to ZSM-11 weight ratio, while Example 12 corresponds to a 26:26 weight ratio. Otherwise, Examples 11 and 12 are similar, with both including 0.03 wt % Pt and a 1:1 molar ratio of Sn to Pt. As shown in Table 5, the higher ratio of meso-mordenite to ZSM-11 provides higher selectivity, C$_{9+}$ conversion, and xylene yield. Examples 13 and 14 are related in a similar manner, and again the higher ratio of meso-mordenite to ZSM-11 in Example 13 provides higher selectivity, C$_{9+}$ conversion, and xylene yield.

As another type of comparison, Table 6 shows a comparison of the impact of varying the ratio of Si to Al$_2$ in the ZSM-11 on catalyst activity. For the examples in Table 6, Example 24 corresponds to a Si to Al$_2$ ratio of roughly 27, Example 8 corresponds to a ratio of roughly 50, and Example 22 corresponds to a ratio of roughly 100.

TABLE 6

Variation of Si/Al$_2$ Ratio in ZSM-11

| Example No. | Aromatic Selectivity | Aged Aromatic Selectivity | C$_{9+}$ Conversion | Aged C$_{9+}$ Conversion | Xylene Yield | Aged Xylene Yield |
|---|---|---|---|---|---|---|
| 24 | 98.4 | 99.08 | 53.32 | 39.88 | 35.04 | 24.71 |
| 8 | 97.39 | 98.40 | 54.8 | 43.73 | 35.32 | 28.18 |
| 22 | 97.15 | 98.51 | 50.41 | 38.56 | 34.86 | 26.13 |

As shown in Table 6, increasing the ratio of Si to Al$_2$ results in decreasing aromatic selectivity. For C$_{9+}$ conversion and xylene yield, the intermediate amount of Si to Al$_2$ results in the highest values.

Examples 34-47: Alternative Supported Metals

A series of catalysts including meso-mordenite, ZSM-11, alumina binder, Pt, and a second metal selected from Mg, Re, Ag, Cu, and Ga were prepared using the following procedure. The amounts of each component in the resulting catalyst are shown in Table 3 below. The relative molar amount of the second metal versus Pt is also shown.

Meso-mordenite crystals from Example 1 were mixed with zeolite crystals and alumina (as a binder) in a muller. Most of the mixtures included the ZSM-11 crystals from Example 2. The exception is Example 30, which contained ZSM-5 from Example 6. The binder is alumina (Versal 300). Addition of an aqueous solution of Tetraammineplatinum chloride and a second salt to provide the second metal in water was added to the muller prior to forming to a desired target loading on the final extrudates of Pt and the second metal. The second salt used was a nitrate salt of the second metal, with the exception of Re, where an Ammonium salt was used. Sufficient water was added to produce an extrudable paste on a 1" extruder, ranging from 49-53% total solids. The mixture of EMM-34, ZSM-11, alumina, and water was extruded into ¹⁄₁₆" cylinder and then dried in a hotpack oven at 121° C. overnight. The dried extrudates were precalcined in nitrogen at 538° C. to decompose and remove the organic template. The precalcined extrudates were then humidified with saturated air at ambient conditions for an hour at 2 cc/g/min. After humidification, the extrudates were exchanged with 1 N ammonium nitrate to remove sodium. The extrudates were then washed with deionized water to remove residual nitrate ions prior to drying at 121° C. for at least 4 hours, followed by calcining in air at 538° C.

TABLE 7

Compositions for Examples 34-47

| Example No. | Meso-Mordenite (wt %) | ZSM-11 (wt %) | Binder (wt %) | Pt (wt %) | Second Metal (wt %) | Second Metal/Pt molar ratio |
|---|---|---|---|---|---|---|
| 34 | 50 | 20 | 30 | 0.026 | Mg 0.02 | 6 |
| 35 | 50 | 20 | 30 | 0.026 | Mg 0.01 | 3 |
| 36 | 40 | 16 | 44 | 0.021 | Mg 0.016 | 6 |
| 37 | 50 | 20 | 30 | 0.026 | Mg 0.03 | 9 |
| 38 | 50 | 20** | 30 | 0.026 | Mg 0.02 | 6 |
| 39 | 50 | 20 | 30 | 0.026 | Re 0.252 | 10 |
| 40 | 50 | 20 | 30 | 0.026 | Re 0.025 | 1 |
| 41 | 50 | 20 | 30 | 0.026 | Re 0.013 | 0.5 |
| 42 | 50 | 20 | 30 | 0.026 | Ag 0.146 | 10 |
| 43 | 50 | 20 | 30 | 0.026 | Ag 0.015 | 1 |
| 44 | 50 | 20 | 30 | 0.026 | Ag 0.007 | 0.5 |
| 45 | 40 | 16 | 44 | 0.021 | Cu 0.041 | 6 |
| 46 | 50 | 20 | 30 | 0.26 | Cu 0.052 | 6 |
| 47 | 50 | 20 | 30 | 0.26 | Ga 0.028 | 3 |

Some of the catalysts in Table 7 were tested under the aromatic conversion conditions in Example 2. The results are shown in Table 8, as indicated by the Example number. The results in Table 8 include aromatic selectivity in the conversion effluent, C$_{9+}$ conversion, and xylene yield. Aging rates for the catalyst activity for both C$_{9+}$ conversion and xylene yield are also provided. For the results in Table 8, the results are reported as index or normalized values in comparison with the results obtained for Comparative Example 6. Thus, the aromatic selectivity, C$_{9+}$ conversion, xylene yield, and the aging rates for Comparative Example 6 are normalized to either 1.0 or 0 (for the aging rates). It is noted that for the aging rates, a negative value represents less aging of the catalyst, so that a negative value means the catalyst is retaining more of the indicated activity over time.

TABLE 8

Aromatic Selectivity, C$_{9+}$ Conversion, and Xylene Yields

| Example No. | Relative Aromatic Selectivity | Relative C$_{9+}$ Conversion | Relative C$_{9+}$ Conversion Aging Rate | Relative Xylene Yield | Relative Xylene Yield Aging Rate |
|---|---|---|---|---|---|
| 6 (Comparative) | 1.0 | 1.0 | +0.0 | 1.0 | +0.0 |
| 34 | 0.98 | 0.99 | +61% | 0.99 | +78% |
| 38 | 0.91 | 0.96 | +38% | 0.94 | +54% |
| 39 | 0.957 | 1.15 | −36% | 1.08 | −39% |
| 42 | 1.001 | 0.97 | −6.6% | 0.87 | +28% |

As shown in Table 8, Example 39 (Pt+Re) had favorable values for relative $C_{9+}$ conversion, relative xylene yield, and relative aging. However, the overall aromatic selectivity was not as favorable. The other catalysts in Table 8 generally had less favorable aging rates.

All numerical values within the detailed description and the claims herein are modified by "about" or "approximately" the indicated value, and take into account experimental error and variations that would be expected by a person having ordinary skill in the art.

While the present invention has been described and illustrated with respect to certain embodiments, it is to be understood that the invention is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed form any pair of an upper preferable value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A method for converting a feedstock comprising $C_{8+}$ aromatics, comprising:
    contacting the feedstock and optionally hydrogen with a catalyst composition under conversion conditions in a reactor comprising at least one fixed catalyst bed of the catalyst composition to produce a converted product mixture, wherein the catalyst composition comprises:
    (i) a mixture of ZSM-11 and mordenite, having a weight ratio of the ZSM-11 to mordenite ranging from 0.25 to 1.2; and
    (ii) a combination of Pt and Sn, having a molar ratio of the Sn to Pt ranging from 1.0 to 10.

2. The method of claim 1, wherein the weight ratio of the ZSM-11 to mordenite is from 0.3 to 1.0.

3. The method of claim 1, wherein the weight ratio of the ZSM-11 to mordenite is from 0.5 to 1.0.

4. The method of claim 1, wherein the catalyst composition comprises 0.005 wt % to 0.1 wt % Pt, based on the total weight of the catalyst composition.

5. The method of claim 1, wherein the catalyst composition comprises 0.005 wt % to 0.02 wt % Pt, based on the total weight of the catalyst composition.

6. The method of claim 1, wherein the catalyst composition further comprises a binder.

7. The method of claim 6, wherein the binder comprises silica.

8. The method of claim 1, wherein feedstock comprises $C_{9+}$ aromatics and at least one of benzene and toluene, and the converted product mixture comprises xylenes.

9. The method of claim 8, wherein the contacting the feedstock with the catalyst composition is effected in the presence of hydrogen.

10. The method of claim 1, wherein the conversion conditions comprise a temperature of from 340° C. to 515° C., a pressure from 380 kPa-a (55 psia) to 4240 kPa-a (615 psia) and a weight hourly space velocity (WHSV) in the range of from 1 to 100 $hr^{-1}$ based on the weight of the feedstock.

* * * * *